(12) United States Patent
Minemura et al.

(10) Patent No.: US 7,026,361 B2
(45) Date of Patent: Apr. 11, 2006

(54) COMPOSITION COMPRISING UBIQUINONE

(75) Inventors: Tsuyoshi Minemura, Iruma-gun (JP); Hironori Kubota, Chiyoda-ku (JP); Shigeo Takagi, Ueda (JP); Yoshiyuki Nishizawa, Hamamatsu (JP)

(73) Assignees: Nisshin Pharma Inc., Tokyo (JP); Freund Industrial Co., Ltd., Tokyo (JP)

( * ) Notice: Subject to any disclaimer, the term of this patent is extended or adjusted under 35 U.S.C. 154(b) by 0 days.

(21) Appl. No.: 10/213,108

(22) Filed: Aug. 7, 2002

(65) Prior Publication Data
US 2003/0105168 A1 Jun. 5, 2003

(30) Foreign Application Priority Data
Aug. 10, 2001 (JP) ............................. 2001-243906

(51) Int. Cl.
*C09K 3/00* (2006.01)
*A61K 9/107* (2006.01)
*A61K 9/14* (2006.01)
*A61K 9/08* (2006.01)
*A23L 1/302* (2006.01)

(52) U.S. Cl. ..................... 516/75; 516/72; 424/94.1; 514/937; 426/72; 426/311

(58) Field of Classification Search ............... 516/72, 516/75; 424/94.1; 514/937; 426/72, 311
See application file for complete search history.

(56) References Cited

U.S. PATENT DOCUMENTS 4,540,602 A * 9/1985 Motoyama et al. ...... 252/363.5
4,751,241 A    6/1988 Motoyama et al. ......... 514/937
4,767,624 A * 8/1988 Okuyama et al. .......... 424/94.1
5,298,246 A * 3/1994 Yano et al. ................ 424/94.1
5,540,942 A * 7/1996 Tokoro ...................... 426/265

FOREIGN PATENT DOCUMENTS

EP   0 522 433    1/1993
JP   57-4916      1/1982
JP   59-51214     3/1984

OTHER PUBLICATIONS

Machine translation of JP 05078240A, Japan Patent Office (6 pages), http://www6.ipdl.jpo.go.jp/Tokujitu/PAJdetail.ipdl?N0000=80&N0120=01&N2001=2&N3001=H05-078240 (Sep. 2003).*
English language Translation of JP 59-161314, PTO-03-[5416], (USPTO, Wash, DC, Sep. 2003), pp. 1-18.*
The Merck Index An Encyclopedia of Chemicals, Drugs, and Biologicals, Tenth Edition, (Merck & Co, Inc. Rahway, NJ, 1983) p. 887, Jan. 17, 1984.*
Hawley's Condensed Chemical Dictionary, Eleventh Edition, edited by Sax and Lewis, Sr. (Van Nostrand Reinhold Company, Ney York, NY, copyright 1987), Oct. 1989, p. 224-225 & 555-556.*

* cited by examiner

*Primary Examiner*—Daniel S. Metzmaier
(74) *Attorney, Agent, or Firm*—Wenderoth, Lind & Ponack, L.L.P.

(57) ABSTRACT

This invention relates to a composition comprising ubiquinone having superior dispersion-stability in an aqueous solution and high bioavailability. The ubiquinone(s) is dispersed and emulsified in an aqueous solution of a water-soluble material in the presence of an organic acid(s) to form a protective colloid, the average particle size of the suspended particles being not more than 5 μm. The liquid composition can be adsorbed in or carried on an excipient, or dried.

9 Claims, No Drawings

COMPOSITION COMPRISING UBIQUINONE

FIELD OF THE INVENTION

This invention relates to a liquid composition comprising ubiquinone which is dispersed and emulsified into an aqueous liquid and has high bioavailability and high dispersion stability. The invention also relates to a solid composition produced from the liquid composition.

BACKGROUND OF THE INVENTION

Ubiquinone is a quinone compound widely distributed over living matters, which is also named a benzoquinone derivative ($CoQ_n$), e.g. 2,3-dimethoxy-5-methyl-6-polyprenyl-1,4-benzoquinone, known as coenzyme Q (CoQ). Among ubiquinones, ubidecarenone ($CoQ_{10}$), which exists in higher animals including humans, is known to have a coenzyme activity as well as a vitamin-like activity to improve the efficiency of oxygen utilization. For this reason, it is thought that a composition comprising ubidecarenone acts on a congested tissue, stabilizes bio-membranes and is effective in antioxidation. The pharmacological effects of ubidecarenone have been clinically accepted for alleviating the symptoms of angina, heart failure, ischemic heart disease, and muscular dystrophy. It has also been reported that ubidecarenone is useful as a curative medicine of the congestive mental disorder (minor or intermediate level) under basic therapy and effective against essential hypertension and gum disease, and effective in preventing side-effects of anticancer drugs and psychotropic drugs, etc.

However, almost all the ubiquinones including ubidecarenone are a lipophilic and fat-soluble solid material with low melting points. It is well known that the absorptivity of ubiquinone by oral administration is low due to its low solubility in water. Ubiquinone is absorbed like fat-soluble vitamins to the living body mainly from lymph vessel. Since the amount to be absorbed is very limited, the bioavailability of ubiquinone is low.

Many attempts have been made to improve the bioabsorptivity and the stability of fat-soluble compositions that are hardly soluble in water. They are dissolved in pharmaceutically acceptable solvents such as vegetable oils, e.g. sesame oil, peanut oil, olive oil, soybean oil, cottonseed oil and corn oil, or in animal oils, e.g. fish liver oil, or dispersed and emulsified in an aqueous liquid with various additives such as an emulsifier, a dispersing agent or a surfactant.

Ubidecarenone compositions were also dissolved in a lipophilic solvent such as vegetable oils or animal oils for oral administration, but satisfactory bioabsorptivity has not been attained. U.S. Pat. No. 4,540,602 discloses dissolving ubidecarenone in a lipophilic solvent and emulsifying it in the presence of a water-soluble material. However the technology is not desirable in that the solvent remains in the final composition and, thus, is not acceptable in view of environmental hygiene or regulation of food additives.

There have been reported methods for promoting the absorption of scarcely soluble drugs containing ubidecarenone from lymph vessel, thereby improving its bioavailability. The scarcely soluble drugs containing ubidecarenone were emulsified with polyglycerol unsaturated fatty acid esters (U.S. Pat. No. 4,751,241), and further with a water-soluble material (JP-A 59-51214). However, a polyglycerol unsaturated fatty acid ester is a high-viscosity liquid substance and, therefore, the amount of the polyglycerol unsaturated fatty acid ester to be added is restricted inevitably, and, as a result, the content of ubidecarenone in the composition is restricted. If the content of ubidecarenone in the composition is low, one time dose or the number of daily administration may increase, which will result in lowered medical compliance and lowered QOL (Quality of Life) of a patient. Thus, it is not desirable. Furthermore, it will be difficult for a patient with lowered deglutition to take an increased dosage of the drug.

European Patent 0522433 discloses administering ubidecarenone emulsified with hydrophilic surfactants such as salt of bile acid, Polysorbate 80, and polyoxyethylene hardened castor oil in order to increase the bioavailability of ubidecarenone. However, use of these hydrophilic surfactants in a large amount may happen to trigger disorders of tunica mucosa ventriculi and alimentary canal membrane such as hemolysis, membrane stimulus and membrane deficit, or hypersensitivity. Therefore, the use of such hydrophilic surfactants is not recommendable.

Moreover, since the melting point of ubidecarenone is as low as 50° C. or so, ubidecarenone may sometimes be dissolved in a solid composition such as powders and tablets, causing colored spots by capillarity or oozing out, which may reduce commercial value of the product.

SUMMARY OF THE INVENTION

An object of this invention is to provide a composition comprising ubiquinone having high bioavailability and high dispersion-stability in an aqueous solution.

Now a liquid composition containing high amount of ubiquinone with high bioavailability and high dispersion-stability in an aqueous solution has been produced by dispersing and emulsifying ubiquinone in an aqueous solution of a water-soluble material in the presence of an organic acid to form a protective colloid.

In one aspect, this invention relates to a composition comprising ubiquinone which is dispersed and emulsified in an aqueous solution of a water-soluble material in the presence of an organic acid(s). To maintain a fine and stable protective colloid, the average size of dispersed particles in the liquid composition is preferably not more than 5 μm, and more preferably not more than 1 μm.

The invention also provides a process of manufacturing the ubiquinone-containing composition which comprises dispersing and emulsifying ubiquinone in an aqueous solution of a water-soluble material in the presence of an organic acid(s) to form a protective colloid.

In another aspect, the invention relates to a ubiquinone-containing composition obtained by allowing the liquid ubiquinone-containing composition to be adsorbed in or carried on an excipient, or drying the liquid composition or removing water from the liquid composition.

DETAILED DESCRIPTION OF THE INVENTION

A ubiquinone means a coenzyme Q having 7–10 isoprene units. The ubiquinone used in this invention is $CoQ_{7-10}$, i.e. $CoQ_7$ (ubiquinone-7), $CoQ_9$ (ubiquinone-9), $CoQ_{10}$ (ubidecarenone) or a mixture thereof, and preferably $CoQ_{10}$ that is an essential component for respiratory chain for higher animals including mammals, and mainly exists in a mitochondrial inner membrane. The amount of ubiquinone in the composition of the invention varies depending upon the formulation, the disease to be treated or prevented with, and the stage of the disease. In case of the liquid composition the amount of ubiquinone is generally 1–30% by weight, preferably 1–25% by weight, e.g. 7% by weight. In case of a solid composition it is 1–30% by weight, preferably 1–10% by weight.

The water-soluble material used in the invention to disperse and emulsify ubiquinone is a material that can form a protective colloid, disperse and emulsify ubiquinone into fine particles and keep the protective colloid homogeneous and stable. Such water-soluble materials include agar, gelatin, xanthane gum, gum arabic, casein, dextrin, sodium carboxymethyl-cellulose (CMC sodium), polyvinyl pyrrolidone (PVP) and water-soluble polysaccharides originated from vegetable, such as corn fiber, starch, guar gum, and pectin. Among them gum arabic from natural plants is specifically suitable because an aqueous solution of gum arabic at a high concentration has comparatively low viscosity and remains mobile and liquid. The amount of water-soluble materials used in the invention varies depending upon the desired content of ubiquinone and the type of water-soluble materials. It generally ranges from 0.1–50% by weight, preferably 3–30% by weight, e.g. 20% by weight, of a final liquid composition.

Organic acids used to disperse and emulsify ubiquinone into the water-soluble material include citric acid, succinic acid, fumaric acid, lactic acid, gluconic acid, malic acid, and/or tartaric acid, preferably malic acid, tartaric acid and a mixture thereof. The amount of organic acids to be added to the liquid composition varies depending upon the kind of the organic acid and generally ranges from 0.5–30% by weight, preferably 1–25% by weight.

For the preparation of the composition of this invention, ubiquinone is first melted and then dispersed and emulsified into an aqueous solution of a water-soluble material in the presence of an organic acid(s) to form a protective colloid having fine particles. For this purpose, it is desirable to prepare an aqueous solution of a water-soluble material and preheat the solution. Into the solution is introduced preheated/melted ubiquinone and the resulting mixture is treated by conventional means, e.g. a high-pressure homogenizer, to be finely dispersed and emulsified until the desired average particle size is obtained, thereby forming a homogeneous and fine protective colloid. These steps are carried out at a temperature higher than the melting point of the ubiquinone, for example, about 30–90° C., preferably 50–70° C. It is also possible to directly add ubiquinone powders into the preheated (about 45–90° C., preferably 50–70° C.) aqueous solution, in which the ubiquinone is melted and dispersed and emulsified to form a protective colloid. This method is advantageous because it increases the process efficiency and can decrease the loss of raw material.

The aqueous protective colloid of a water-soluble material thus formed is advantageous in that it stably maintains finely dispersed particles of ubiquinone and as a result accelerates the intake through alimentary canal wall.

According to an embodiment of the invention, a solid composition can be produced by allowing the ubiquinone-containing composition to be adsorbed in or carried on an excipient. Any type of excipients capable of adsorbing or carrying the liquid emulsified composition and acceptable for the oral administration can be used for this purpose. Examples are powdered lactose, microcrystalline cellulose, β-cyclodextrin, sugar (including monosccharide, oligosaccharide, polysaccharide like starch, dextrin, and enzymatically decomposed dextrin), finely powdered silicon dioxide, sugar alcohol and the like.

Moreover, the functionality and characteristics of the solid composition can be changed according to the selection of the excipient. For example, if sorbitol, dextrin and/or mannitol are used as an excipient, the solid composition becomes soluble in water. If lactose, cornstarch, sorbitol, and/or crystalline cellulose are used, the solid composition acquires plasticity and can be directly compacted into tablet. Moreover, chewable tablets, differentially soluble tablets, foaming tablets and the like can be prepared accordingly.

An example of the method for producing the solid composition of this invention is a fluidized bed granulation method, in which the liquid composition of the invention is sprayed onto a fluidized bed of the excipient fluidized by an ascending current preheated at a required temperature and the mixture is dried. Another example is a stirring granulation method, in which the liquid composition is dropwise added or sprayed onto the excipient at least a part of which is being stirred by a stirring fan. Any other suitable methods can be used.

Alternatively, the solid composition of this invention can be produced by removing water/moisture from the liquid composition and then physically mixing a dried powder thus obtained with any excipient mentioned above.

The compositions produced as mentioned above, either by directly drying it or by adsorbing it in an excipient or by carrying it on an excipient, have been dispersed and emulsified at the time of forming the protective colloid with an average particle size not more than 5 μm, preferably not more than 1 μm. And therefore they are promptly re-dispersed to fine particles when administered.

Furthermore, for preparing the solid composition, any conventional auxiliaries such as a binder, a disintegrator, a dispersant, an antiseptic and a lubricant can be used. For example, the binder used in this invention is preferably a water-soluble binder such as polyvinylpyrrolidone, hydroxypropyl cellulose, polyvinyl alcohol, hydroxypropyl methylcellulose, methylcellulose, Pullulan, syrup, sodium arginate, agar, gelatin, soybean polysaccharide, gum arabic and the like.

The composition of the invention prepared as mentioned above comprises ubiquinone in an amount of 1–25% by weight, a water-soluble material in an amount of 3–30% by weight, an organic acid(s) in an amount of 1–25% by weight and water to make 100%. The solid composition comprises ubidecarenone in an amount of 1–50% by weight, a water-soluble material in an amount of 1–50% by weight, an organic acid(s) in an amount of 1–30% by weight and an excipient in an amount of 0–97% by weight.

EXAMPLES

Hereafter, the invention is illustrated by examples which by no means restrict the invention.

Example 1

Five grams of ubidecarenone (produced by Nisshin Pharma Co. Ltd.) was heated to 60° C. and melted. It was then dispersed and emulsified in an aqueous protective colloid which had been prepared in advance and heated to 60° C. containing 1 g of malic acid, 5 g of gum arabic (Sankyo Food) and 89 g of water in a homogenizer (1000 rpm, 3 minutes). The emulsion was further passed through a high-pressure homogenizer (processing pressure of 1000 kg/cm$^2$, 2 times) to form a fine and homogeneous protective colloid (liquid composition). The particle diameter of the dispersed and emulsified particles in the resulting protective colloid was measured by a particle size distribution measuring device (MICROTRAC FRA; Nikkiso Co. Ltd.) using the laser diffraction/scattering method. 50% particle size was 0.95 µm. The protective colloid was sprayed into air stream heated at 130° C. to remove water/moisture, thereby affording an orange-colored powder composition (solid composition).

Example 2

250 g of ubidecarenone and 125 g of malic acid were introduced into an aqueous protective colloid which had been prepared and heated to 60° C. containing 600 g of gum arabic and 4,000 g of water, and the emulsion was passed through a high-pressure homogenizer (processing pressure of 750 kg/cm$^2$, 3 times) to form a fine and homogeneous protective colloid. The particle size of the dispersed and emulsified particles in the protective colloid was measured as in Example 1, 50% particle size being 0.61 µm.

Example 3

Into a mixture of excipients consisting of 2,500 g of lactose, 1,150 g of sorbitol and 500 g of dextrin and being fluidized by a fluidized bed granulator (FLO-5, Freund Industry), the protective colloid prepared in Example 2 was sprayed to give an orange-colored powder-granule composition (solid composition). After being stored at 40° C. and 50° C. for one month, the composition retained good water dispersibility without causing a color-spot or oozing from the melted ubidecarenone.

Example 4

50 g of ubidecarenone and 12.5 g of malic acid were introduced into an aqueous protective colloid containing 125 g of gelatin (AP-100, Nitta Gelatin) and 1,000 g of water, which had been prepared in advance and heated to about 60° C., and allowed to be emulsified. The emulsion was passed through a high-pressure homogenizer under the same conditions as in Example 2 to form a fine and homogeneous protective colloid. The diameter of particles in the protective colloid was measured as in Example 1, 50% particle size being 0.44 µm.

Example 5

50 g of ubidecarenone and 12.5 g of malic acid were introduced into an aqueous protective colloid containing 125 g of water-soluble corn starch (CELLUACE, Japan Maize Products Co., Ltd.) and 1,000 g of water, which had been prepared in advance and heated to about 60° C., and allowed to be emulsified. The emulsion was passed through a high-pressure homogenizer under the same conditions as in Example 2 to form a fine and homogeneous protective colloid. The diameter of particles in the protective colloid was measured as in Example 1, 50% particle size being 0.44 µm.

Example 6

50 g of ubidecarenone and 12.5 g of malic acid were introduced into an aqueous protective colloid containing 125 g of processed starch (LMASTER, Matsutani Chemical) and 1,000g of water, which had been prepared in advance and heated to about 60° C., and allowed to be emulsified. The emulsion was passed through a high-pressure homogenizer under the same conditions as in Example 2 to form a fine and homogeneous protective colloid. The diameter of particles in the protective colloid was measured as in Example 1, 50% particle size being 0.36 µm.

Example 7

50 g of ubidecarenone and 12.5 g of malic acid were introduced into an aqueous protective colloid preheated to 60° C. and consisting of 125 g of gum arabic and 1,000 g of water, and allowed to be emulsified. The emulsion was passed through a high-pressure homogenizer under the same conditions as in Example 2 to form a fine and homogeneous protective colloid. Then it was sprayed onto a fluidized bed of a mixture of excipients consisting of 462.5 g of lactose and 350 g of dextrin in a fluidized bed granulator (FL-LABO, Freund Industrial) to produce an orange-yellow composition in powder-granule form.

Example 8

50 g of ubidecarenone and 12.5 g of tartaric acid were introduced into an aqueous protective colloid preheated to 60° C. and consisting of 125 g of gum arabic and 1,000 g of water, and allowed to be emulsified. The emulsion was passed through a high-pressure homogenizer under the same conditions as in Example 2 to form a fine and homogeneous protective colloid. The protective colloid was sprayed onto a fluidized bed of a mixture of excipients consisting of 462.5 g of lactose and 350 g of dextrin in a fluidized bed granulator (FL-LABO, Freund Industrial) to produce an orange-yellow composition in powder-granule form.

Comparative Example 1

50 g of ubidecarenone was introduced into an aqueous protective colloid consisting of 125g of gum arabic and 1,000g of water, which had been heated to 60° C. in advance, and allowed to be emulsified. The emulsion was passed through a high-pressure homogenizer under the same conditions as in Example 2 to form a fine and homogeneous protective colloid. Then it was sprayed onto a fluidized bed of a mixture of excipients consisting of 500 g of lactose and 350 g of dextrin fluidized in a fluidized bed granulator (FL-LABO, Freund Industrial) to produce an orange-yellow composition in powder-granule form.

Stability Test

The compositions produced in Examples 7–8 and Comparative Example 1 were tested for (a) the residual ratio of ubidecarenone and (b) the production of decomposed ubidecarenone as follows:

1) Preservation Conditions

Preserved at 50° C. in a sealed glass bottle container for a period of zero to 6 weeks.

2) Method of Measurement

Measurement of ubidecarenone, ubichromenol and other decomposed products was carried out by HPLC under the following conditions:

Detector; ultraviolet absorption photometer (measurement wavelength: 275 nm)
Column; Hypersil ODS-5 4.6 mm×15 cm
Mobile phase; methanol/absolute ethanol (13:7)

Based on the measured value of each substance by HPLC were calculated (a) the residual ratio of ubidecarenone, and (b) the production ratios of the decomposed substances. Table 1 shows the former and Table 2 shows the latter.

TABLE 1

The residual ratio of ubidecarenone (%)

| | Preservation period (week) | | | |
|---|---|---|---|---|
| Sample | 0 | 2 | 4 | 6 |
| Comparative Example 1 | 100.0 | 98.2 | 95.7 | 91.3 |
| Example 7 | 100.0 | 99.9 | 100.6 | 100.2 |
| Example 8 | 100.0 | 99.7 | 99.9 | 99.8 |

TABLE 2

The production ratio of decomposed substances (%)

| | 2 Weeks | | 4 Weeks | | 6 Weeks | |
|---|---|---|---|---|---|---|
| Sample | Ubichromenol | Other decom. products | Ubichromenol | Other decom. products | Ubichromenol | Other decom. products |
| Comparative Example 1 | 0.15 | 0.10 | 0.26 | 0.23 | 0.48 | 0.62 |
| Example 7 | NT | 0.01 | NT | 0.03 | NT | 0.06 |
| Example 8 | NT | 0.02 | NT | 0.05 | NT | 0.08 |

*NT = not detected (c) Stability test of the protective colloid In 50 ml of water was dispersed each 1 g of the powder solid compositions used in testing (a) and (b) mentioned above, and the average particle size in the dispersion liquid was measured by a wet process using Micro Track (Nikkiso Co., Ltd., a laser diffraction type particle size measurement equipment). The dispersion liquid was centrifuged (2500 rpm, 5 minutes) and separation/precipitation of the dispersion liquid was inspected visually. The results are shown in the following Table 3.

The upper row shows the average particle size (μm). The lower row shows the results of visual evaluation of the dispersion liquid after the centrifugation based on the following standard:

−: No separation was observed
+: A little sediment was observed
++: Plenty of sediment was observed

TABLE 3

| | Preservation period (week) | | | |
|---|---|---|---|---|
| Sample | 0 | 2 | 4 | 6 |
| Comparative Example 1 | 0.843 — | 0.874 — | 0.952 — | 0.931 — |
| Example 7 | 0.885 — | 0.893 — | 0.901 — | 0.892 — |
| Example 8 | 0.924 — | 0.977 — | 0.996 — | 0.993 — |

As shown in Tables 1–3, the compositions of Examples 7 and 8 using an organic acid maintained good dispersibility and favorable average particle size, and showed no decrease of ubidecarenone and remarkably low leveled decomposed products over a long time preservation. On the other hand, the composition of Comparative Example 1, in which ubidecarenone was dispersed and emulsified in the absence of an organic acid, maintained good dispersibility and favorable average particle size during a long time storage, but showed the decrease of ubidecarenone and the increase of the decomposed products. This shows a problem in view of stability.

INDUSTRIAL APPLICABILITY

The liquid or solid composition comprising ubiquinone according to the invention has superior dispersion-stability in an aqueous solution, superior storage stability and high bioavailability. These compositions maintain not only long-term dispersibility but also remarkably low level in decomposition and high stability of ubiquinone. For these reasons, the compositions of the invention are very useful not only as medicines but also as health foods or materials for food industry.

What is claimed is:

1. A stabilized composition consisting of ubiquinone, water, a water-soluble material(s) selected from the group consisting of gum arabic, agar, water-soluble corn fiber, starch, dextrin and polyvinylpyrrolidone, and an organic acid(s) selected from the group consisting of succinic acid, fumaric acid, lactic acid, gluconic acid, malic acid and tartaric acid which is produced by dispersing and emulsifying ubiquinone in an aqueous liquid consisting of water, the water-soluble material(s) and the organic acid(s) to form the stabilized composition.

2. The composition of claim 1, wherein the ubiquinone is ubidecarenone.

3. The composition of claim 1, which is in the form of dispersed particles with an average particle size of not more than 5 μm.

4. The composition of claim 1, wherein the water-soluble material is gum arabic.

5. A stabilized composition consisting of ubiquinone, an excipient(s), a water-soluble material(s) selected from the group consisting of gum arabic, agar, water-soluble corn fiber, starch, dextrin and polyvinylpyrrolidone, and an organic acid(s) selected from the group consisting of succinic acid, fumaric acid, lactic acid, gluconic acid, malic acid and tartaric acid which is produced by dispersing and emulsifying ubiquinone in an aqueous liquid consisting of water, the water-soluble material(s) and the organic acid(s), allowing the resultant composition to be adsorbed in or carried on an excipient(s) and drying to form the stabilized composition.

6. A stabilized composition consisting of ubiquinone, a water-soluble material(s) selected from the group consisting of gum arabic, agar, water-soluble corn fiber, starch, dextrin and polyvinylpyrrolidone, and an organic acid(s) selected from the group consisting of succinic acid, fumaric acid, lactic acid, gluconic acid, malic acid and tartaric acid which is produced by dispersing and emulsifying ubiquinone in an aqueous liquid consisting of water, the water-soluble material(s) and the organic acid(s) and drying the resultant composition to form the stabilized composition.

7. A process for producing a stabilized composition consisting of ubiquinone, water, a water-soluble material(s) selected from the group consisting of gum arabic, agar, water-soluble corn fiber, starch, dextrin and polyvinylpyrrolidone, and an organic acid(s) selected from the group consisting of succinic acid, fumaric acid, lactic acid, gluconic acid, malic acid and tartaric acid which consists of dispersing and emulsifying ubiquinone in an aqueous liquid consisting of water, the water-soluble material(s) and the organic acid(s) to form the stabilized composition.

8. A process for producing a stabilized composition consisting of ubiquinone, an excipient(s), a water-soluble material(s) selected from the group consisting of gum arabic, agar, water-soluble corn fiber, starch, dextrin and polyvinylpyrrolidone, and an organic acid(s) selected from the group consisting of succinic acid, fumaric acid, lactic acid, gluconic acid, malic acid and tartaric acid, which consists of dispersing and emulsifying ubiquinone in an aqueous liquid consisting of water, the water-soluble material(s) and the organic acid(s), allowing the resultant composition to be absorbed in or carried on the excipient(s) and drying to form the stabilized composition.

9. A process for producing a stabilized composition consisting of ubiquinone, a water-soluble material(s) selected from the group consisting of gum arabic, agar, water-soluble corn fiber, starch, dextrin and polyvinylpyrrolidone, and an organic acid(s) selected from the group consisting of succinic acid, fumaric acid, lactic acid, gluconic acid, malic acid and tartaric acid, which consists of dispersing and emulsifying ubiquinone in an aqueous liquid consisting of water, the water-soluble material(s) and the organic acid(s) and drying the resultant composition to form the stabilized composition.

* * * * *